(12) United States Patent
Kleinjans et al.

(10) Patent No.: US 8,278,044 B2
(45) Date of Patent: Oct. 2, 2012

(54) METHOD FOR THE IDENTIFICATION OF CARCINOGENIC COMPOUNDS

(75) Inventors: Joseph Catharine Stephanus Kleinjans, Maastricht (NL); Joseph Henri Marie Delft, Maastricht (NL)

(73) Assignees: Universiteit Maastricht, Maastricht (NL); Academisch Ziekenhuis Maastricht, Maastricht (NL)

( * ) Notice: Subject to any disclaimer, the term of this patent is extended or adjusted under 35 U.S.C. 154(b) by 0 days.

(21) Appl. No.: 12/998,915

(22) PCT Filed: Dec. 17, 2009

(86) PCT No.: PCT/EP2009/067436
§ 371 (c)(1),
(2), (4) Date: Jun. 15, 2011

(87) PCT Pub. No.: WO2010/070059
PCT Pub. Date: Jun. 24, 2010

(65) Prior Publication Data
US 2011/0250606 A1 Oct. 13, 2011

(30) Foreign Application Priority Data
Dec. 17, 2008 (EP) .................................. 08171935

(51) Int. Cl.
*C12Q 1/68* (2006.01)

(52) U.S. Cl. ........................ 435/6.1; 435/6.11; 435/6.12

(58) Field of Classification Search ................ 435/6, 6.1, 435/6.11, 6.12
See application file for complete search history.

(56) References Cited

U.S. PATENT DOCUMENTS

| | | | |
|---|---|---|---|
| 5,811,231 A | 9/1998 | Farr et al. | |
| 6,228,589 B1 | 5/2001 | Brenner | |
| 6,713,261 B1 | 3/2004 | Pallardy et al. | |
| 2003/0203388 A1 | 10/2003 | Aubrecht | |
| 2004/0197855 A1 | 10/2004 | Wiesmuller | |
| 2007/0224609 A1 | 9/2007 | Hastwell et al. | |
| 2007/0269824 A1 | 11/2007 | Albrecht et al. | |
| 2008/0138820 A1 | 6/2008 | Thomas | |

FOREIGN PATENT DOCUMENTS

| WO | WO 97/13877 | 4/1997 |
|---|---|---|
| WO | WO 2005/081783 | 9/2005 |
| WO | WO 2006/056340 | 6/2006 |
| WO | WO 2006/055676 | 7/2006 |
| WO | WO 2007/073774 | 7/2007 |
| WO | WO 2010/070059 A1 | 6/2010 |

OTHER PUBLICATIONS

Shivji et al.; Proliferating cell nuclear antigen is required for DNA excision repair; Cell; vol. 69, No. 2; pp. 367-374; published Apr. 17, 1992.*
PCT International Preliminary Report on Patentability, PCT/EP2009/067436 dated Jun. 21, 2011.
Ellinger-Ziegelbauer et al., Comparison of the Expression Profiles Induced by Genotoxic and Nongenotoxic Carcinogens in Rat Liver, Mutation Research, Aug. 4, 2005, pp. 61-84, vol. 575, No. 1-2, Elsevier, Amsterdam, NL.
Hu et al., Identification of a Gene Expression Profile That Discriminates Indirect-Acting Genotoxins From Direct-Acting Genotoxins, Mutation Research, May 18, 2004, pp. 5-27, vol. 549, No. 1-2, Elsevier, Amsterdam, NL.
Uehara T et al., A Toxicogenomics Approach for Early Assessment of Potential Non-Genotoxic Hepatocarcinogenicity of Chemicals in Rats Toxicology, Limerick, IR, vol. 250, No. 1, Aug. 19, 2008, pp. 15-26.
Luo et al., Phenotypic Anchoring of Global Gene Expression Profiles Induced by N-Hydroxy-4-Acetylaminobiphenyl and Benzo[A]Pyrene Dial Epoxide Reveals Correlations Between Expression Profiles and Mechanism of Toxicity, Chemical Research in Toxicology, pp. 619-629, Apr. 2005, vol. 18, No. 4.
Van Delft et al., Comparison of Supervised Clustering Methods to Discriminate Genotoxic From Non-Genotoxic Carcinogens by Gene Expression Profiling, Mutation Research, Amsterdam, NL, Aug. 4, 2005, pp. 17-33, vol. 575, No. 1-2.
Liu X et al., Development of a Highthroughput Yeast-Based Assay for Detection if Metabolically Activated Genotoxins, Mutation Research. Genetic Toxicology and Environmental Mutagenesis, May 31, 2008, pp. 63-69, vol. 653, No. 1-2, Elsevier, Amsterdam, NL.
Wood et al., Human DNA Repair Genes, Science, vol. 291, No. 5507, Feb. 16, 2001, pp. 1284-1289, American Association for the Advancement of Science, US, Washington, DC.
Combes et al., An Analysis of the Efficacy of Bacterial DNA-Repair Assays for Predicting Genotoxicity, Mutation Research, Mar. 1, 1983, pp. 81-92, vol. 108, No. 1-3, Elsevier, Amsterdam, NL.
PCT International Search Report and Written Opinion, PCT/EP2009/067436, dated Mar. 4, 2010.

* cited by examiner

*Primary Examiner* — Michele K Joike
*Assistant Examiner* — Antonio Galisteo Gonzalez
(74) *Attorney, Agent, or Firm* — TraskBritt (57) ABSTRACT

The present invention relates to methods for the identification of genotoxic carcinogenic compounds. In particular, a method is disclosed for the identification of genotoxic carcinogenic compounds wherein a eukaryotic cell is exposed to a potentially genotoxic compound in a culture medium where after samples are taken from the cell and/or the culture medium at least one predetermined time point which samples are then analysed for increased or decreased expression levels of at least three DNA repair genes as compared to a control cell that is not exposed to the carcinogenic compound.

3 Claims, 2 Drawing Sheets

METHOD FOR THE IDENTIFICATION OF CARCINOGENIC COMPOUNDS

CROSS-REFERENCE TO RELATED APPLICATIONS

This is a national phase entry under 35 U.S.C. §371 of international Patent Application PCT/EP2009/067436, filed Dec. 17, 2009, published in English as International Patent Publication WO 2010/070059 A1 on Jun. 24, 2010, which claims the benefit under Article 8 of the Patent Cooperation Treaty to European Patent Application Serial No. 08171935.3, filed Dec. 17, 2008, the entire disclosure of each of which is hereby incorporated herein by this reference.

FIELD OF THE INVENTION

The present invention relates to methods for the identification of genotoxic carcinogenic compounds.

BACKGROUND OF THE INVENTION

Chemicals can cause cancer through a variety of mechanisms. Genotoxic carcinogenic compounds may lead to damage of the genetic material, either directly by covalently binding to DNA or indirectly by interfering with the mitotic machinery, ultimately leading to mutations in genes or large aberrations in chromosomes (Hayashi, Y. (1992) Overview of genotoxic carcinogens and non-genotoxic carcinogens Exp Toxicol Pathol 44, 465-71). Genotoxic carcinogenic compounds are also often called genotoxic carcinogens and their mode of action is also referred to as genotoxicity.

If tumour suppressor genes are inactivated or proto-oncogenes are activated by this process, this may lead to uncontrolled growth of cells, in particular to cancer formation. The mode of action of non-genotoxic carcinogens can be very diverse, but does not include damage to DNA or chromosomes, and may involve stimulation of cell proliferation, suppression of apoptosis, induction of oxidative stress, activation of biotransformation enzymes, suppression of the immune system, etc (Shaw, I. C. & Jones, H. B. (1994) Mechanisms of non-genotoxic carcinogenesis Trends Pharmacol Sci 15, 89-932).

Polycyclic aromatic hydrocarbons (PAH) comprise of a large group of structurally related compounds, of which many are carcinogens. Humans are daily exposed to PAH as they are widely present in the environment and in food. Many carcinogenic PAH, such as benzo[a]pyrene (BaP), share both genotoxic and non-genotoxic properties.

During several enzymatic steps involving cytochrome P450 enzymes and epoxide hydroxylase, BaP is converted into the ultimate genotoxic carcinogen benzo[a]pyrene-7,8-dihydrodiol-9,10-epoxide (BPDE). BPDE can react with nucleophylic groups in DNA, thereby forming DNA adducts, mainly consisting of BPDE-N2deoxyguanosin (BPDE-dG) (Cheng, S. C., Hilton, B. D., Roman, J. M. & Dipple, A. (1989) DNA adducts from carcinogenic and noncarcinogenic enantiomers of benzo[a]pyrene dihydrodiol epoxide Chem Res Toxicol 2, 334-40). If not removed by DNA repair systems, these adducts lead to mutations during replication (Moriya, M., Spiegel, S., Fernandes, A., Amin, S., Liu, T., Geacintov, N. & Grollman, A. P. (1996) Fidelity of translesional synthesis past benzo[a]pyrene diol epoxide-2'-deoxyguanosine DNA adducts: marked effects of host cell, sequence context, and chirality Biochemistry 35, 16646-51). BaP can also be transformed into radical cations by CYP peroxidase (Cavalieri, E. L. & Rogan, E. G. (1995) Central role of radical cations in metabolic activation of polycyclic aromatic hydrocarbons Xenobiotica 25, 677-88), and into reactive and redox-active o-quinones involving aldo-kto reductases, which also can form stable and depurinating DNA adducts (Penning, T. M., Burczynski, M. E., Hung, C. F., McCoull, K. D., Palackal, N. T. & Tsuruda, L. S. (1999) Dihydrodiol dehydrogenases and polycyclic aromatic hydrocarbon activation: generation of reactive and redox active o-quinones Chem Res Toxicol 12, 1-18 and Balu, N., Padgett, W. T., Lambert, G. R., Swank, A. E., Richard, A. M. & Nesnow, S. (2004) Identification and characterization of novel stable deoxyguanosine and deoxyadenosine adducts of benzo[a]pyrene-7,8-quinone from reactions at physiological pH Chem Res Toxicol 17, 827-38). Auto-oxidation of the intermediate catechols and/or subsequent redox cycling of the o-quinones generates reactive oxygen species (ROS) capable of modifying DNA, leading to the formation of oxidised nucleotides like 8-hydroxy-deoxyguanosine (8-OHdG) (Caino, M. C., Oliva, J. L., Jiang, H., Penning, T. M. & Kazanietz, M. G. (2007) Benzo[a]pyrene-7,8-dihydrodiol promotes checkpoint activation and G2/M arrest in human bronchoalveolar carcinoma H358 cells Mol Pharmacol 71, 744-50). These processes all comprise the genotoxic properties of BaP.

Cisplatin is another genotoxic carcinogenic agent that is often used as a chemotherapeutic agent in the treatment of cancer. Cisplatin damages DNA by forming DNA-protein cross-links. See, Costa, M., et al. (1997) J. Toxicol. Environ. Health 50(5), 433-449; and Zhitkovich, A. and Costa, M. (1992) Carcinogenesis 13(8), 1485-1489.

Genetic toxicology testing in the pharmaceutical industry provides an assessment of genotoxic risk associated with the use of drugs. Since the beginning of genotoxicity testing in the early 1970s, many different test systems have been developed and used. No single conventional test is capable of detecting all genotoxic agents. Therefore, genotoxic evaluation of pharmaceutical compounds involves the use of a standard battery of in vitro and in vivo assays. See ICH (1997) Harmonized tripartite guideline, genotoxicity: a standard battery for genotoxicity testing of pharmaceuticals. Recommendations for adoption at step 4 of the ICH process on July 1997 by the ICH Steering Committee (final draft). These tests include bacterial reverse-mutation tests, in vitro tests for chromosomal damage (e.g., cytogenetic assays and in vitro mouse lymphoma thymidine kinase assay) and in vivo tests for chromosomal damage (e.g., rodent micronucleus test).

Molecular biology and recombinant technology provide additional methods by which genotoxicity may be measured. For example, differential gene expression technology may be used to study changes in gene expression of cells exposed to drug and chemical substances. Differential gene expression may be measured using various techniques known to those with skill in the art, including, gel electrophoresis and polynucleotide microarrays.

Genotoxic stress triggers a variety of biological responses including the transcriptional activation of genes regulating DNA repair, cell survival and cell death. Factors that may cause genotoxic stress include exposure to chemical and biological agents and radiation.

GADD45 has been identified as a gene that is induced by DNA damaging factors such as ultraviolet and gamma radiation, the alkylating agent, methyl methanesulfonate (MMS), N-acetoxy-2-acetylaminofluorine and hydrogen peroxide. See; Fornace, A. J., et al. (1988) Proc. Natl. Acad. Sci. USA 85, 8800-8804; Papathanasiou, M. A., et al. (1991) C. Mol. Cell. Biol. 11, 1009-1016; and Takekawa, M. and Saito H. (1998) Cell 95(4), 521-530.

US2007224609 relates to methods for detecting for the presence of an agent that putatively causes or potentiates DNA damage comprising subjecting a cell to an agent; and monitoring the expression of the reporter protein from the cell. The cells as used therein contain a DNA sequence encoding a reporter protein operatively linked to a human GADD45alpha gene promoter and a human GADD45alpha gene regulatory element arranged to activate expression of the DNA sequence in response to DNA damage. The invention also concerns expression cassettes, vectors and cells which may be used according to such a method and also modified media that may be employed in fluorescence assays and in preferred embodiments of the method of the invention.

Aubrecht, J., et al. (1999) Toxicol. Appl. Pharmacol. 154 (3), 228-235 discloses that metallocene molecules containing vanadium, although structurally similar to cisplatin and causing cytotoxicity via apoptosis as does cisplatin, do not cause DNA double strand breaks measured by the yeast DEL recombination assay and do not activate GADD45 promoter activity.

WO 97/13877 and related U.S. Pat. No. 6,228,589 disclose methods for assessing the toxicity of a compound in a test organism by measuring gene expression profiles of selected tissues.

U.S. Pat. No. 5,811,231 describes methods and diagnostic kits for identifying and characterizing toxic compounds, wherein the methods and kits measure transcription or translation levels from genes linked to native eukaryotic stress promoters.

Rockett, John C., et al. (2000) Xenobiotica 30, 155-177 describes DNA arrays and methods of preparing and using DNA arrays and various applications for which DNA arrays may be used, including toxicological applications.

US2008138820 describes a method for determining the effect of a test agent on a phenotypic property of a specific cell expressing a number of reporter genes responsive to the test agent.

WO2006056340 describes a method for determining the genotoxicity of a test compound, said method comprising the steps of contacting a viable test cell with said test compound and determining the change in expression level of an indicator gene selected from the group consisting of Prelp (Proline arginine-rich end leucine-rich repeat); Sesn2 (Sestrin 2); 4833427G06 Rik (RIKEN cDNA); Dda3 (Differential display and activated by p53); Usp30 (Ubiquitin specific protease 30); 0610013D04 Rik (RIKEN cDNA); Slc19a2 (Solute carrier family 19 (thiamine transporter, member 2); Trp53inp1 (Transformation related protein 53, inducible nuclear protein 1); D4Ertd421e (DNA segment, Chr 4, ERATO Doi 421, expressed); Shcbp1 (She SH2-domain binding protein 1); MM67 (Antigen identified by MAb Ki67); Phex (Phosphate regulating neutral endo-peptidase (X chromosome)); Tk1 (Thymidine kinase 1); Mmhead (*Mus musculus* 15 day embryo head cDNA clone); Osbpl6 (Oxysterol binding protein-like 6); Mphosph1 (M-phase phosphoprotein); Ephx1 (Epoxide hydrolase 1 (microsomal xenobiotic hydrolase)); Top2a (Topoisomerase (DNA) II alpha); Ccng1 (Cyclin G1); Plf (Proliferin); Np95 (Nuclear protein 95); Rad51ap1 (RAD51-associated protein 1); Nos3 (Nitric oxide synthase 3, endothelial cell); 2610005B21 Rik (RIKEN cDNA); Brca1 (Breast cancer 1); Stk18 (Serine/threonine kinase 18); Calmbp1 (Calmodulin binding protein 1); Lek1 (Leucine, glutamic acid, lysine family 1 protein); Smc2U (SMC2 structural maintenance of chromosomes 2-like 1); E2f7 (E2F transcription factor 7); Hmmr (Hyaluronan mediated motility receptor (RHAMM)); Nusap1 (Nucleolar and spindle associated protein 1); Fbxo5 (f-box only protein 31); Slc19a2 (Solute carrier family 19 (thiamine transporter), member 2); 9030617003 Rik (RIKEN cDNA); Ly6e (Lymphocyte antigen 6 complex, locus E); 6530401 L14 Rik (RIKEN cDNA); Mad3 (Max dimerization protein 3); Hmgb2 (High mobility group box 2); Kifl1 (Kinesin 11); Mad2ll (MAD2 (mitotic arrest deficient, homolog)-like 1 (yeast)); Asflb (ASFI anti-silencing function 1 homolog B (Saccharomyces)); Mcm3 (Minichromosome maintenance deficient 3 (Saccharomyces)); MGC: 32192 (Mus musculus cDNA clone MGG32192 IMAGE:5006129); Foxm1 (Forkhead box MI); Anxa8 (Annexin A8); Slc35a5 (Solute carrier family 35, member A5); E030024M05 Rik (RIKEN cDNA); Cks2 (CDC28 protein kinase regulatory subunit 2); Cilp (Cartilage intermediate layer pro); Tacc3 (Transforming, acidic coiled-coil containing protein 3); Prc1 (Protein regulator of cytokinesis 1); 2610509G12 Rik (RIKEN cDNA); 2810417H13 Rik (RIKEN cDNA); Pbk (PDZ binding kinase); Capn[beta] (Calpain 6); Gmnn (Geminin); Mcmd4 (Minichromosome maintenance deficient 4 homolog); Ccna2 (Cyclin A2); Pola1 (DNA polymerase alpha 1, 180 kDa); Hmgb3 (High mobility group box 3); Tagln (Transgelin (smooth muscle 22 protein)); 1600013K19 Rik (RIKEN cDNA); Serpine1 (Ser (or Cys) proteinase inhibitor, clade E, member 1); Wig1 (Wild-type p53-induced gene 1); Hgf (Hepatocyte growth factor (scatter factor)); Gnpi (Glucosamine-6-phosphate deaminase); Birc5 (Baculoviral IAP repeat-containing 5); Prim1 (DNA primase, p49 subunit); Rbl1 (Retinoblastoma-like 1 (plO7)); Pcna (Proliferating cell nuclear antigen); E130315B21 Rik (RIKEN cDNA); 2610019103 RIK (RIKEN cDNA); wherein an increase in expression of at least 1.5-fold indicates that said test compound exhibits genotoxicity.

WO2007073774 concerns the use of P130Cas/BCAR1 protein and/or encoding gene for the screening for substances useful in the treatment of tumors. It also concerns a method for the diagnosis of malignant cell growth comprising the measuring the expression of P130Cas/BCAR1 gene. It also concerns non-human transgenic animals as model study for human pathologies, preferably cancer, being transgenic for having altered P130Cas/BCAR1 and Neu-T expression.

WO2005081783 provides a method of detecting exposure to a genotoxic agent in a live subject, comprising the steps of collecting a sample from said subject and detecting the presence of FANCD2-containing foci in said sample, wherein the presence of foci is indicative of exposure to a genotoxic agent.

Patent application UA14610U describes a method for detecting genotoxic and cytotoxic action of antihelminthics which comprises the steps of treating a biological test object with a preparation and a subsequent analysis of samples taken from the test object. Cells of mouse marrow and pig blood lymphocytes are used as the test objects. DNA is extracted from the cell suspensions and analysed for damages using gel electrophoresis.

US2004197855 discloses a process for the determination of genotoxicities characterised in that cells comprising a set of fluorescent or luminescent selection markers are brought into contact with a test compound, wherein the appearance, increase, or decrease in fluorescent or luminescent cells corresponding to the activity of the wild-type gene product of the selection markers indicates the genotoxic effect of the test compound.

US2003203388 deals with a method of characterizing an agent, comprising the steps of treating a mammal cell or a mammal with an agent; and characterizing the DNA-interacting genotoxicity of said agent by determining the effect of said agent on expression in said mammal cell or mammal of at least one gene selected from the group consisting of genes with accession numbers X54149, 000937, AV138783, A1847051, AF055638, A1461837.

U.S. Pat. No. 6,713,261 discloses a method for assessing in vitro the genotoxicity of a compound, which consist in contacting said compound with at least a cell or cell type over-expressing bcl2 protooncogene and/or related anti-apoptotic protein, and observing the genotoxic effects of said compound on said cell.

In spite of all the above described methods, there exists a need to further identify, characterize and understand the mechanism of action of toxicologically relevant genes in order to simplify the development, screening, and testing of new drug and chemical substances.

SUMMARY OF THE INVENTION

One aspect of this invention provides a method for the identification of genotoxic carcinogenic compounds wherein a eukaryotic cell is exposed to a potentially genotoxic compound in a culture medium where after samples are taken from the cell and/or the culture medium at least one predetermined time point which samples are then analysed for increased or decreased expression levels of at least one DNA repair gene as compared to a control cell that is not exposed to the carcinogenic compound.

In a preferred embodiment of the invention, said identification of genotoxicity comprises characterizing said agent a DNA-interacting genotoxic compound, preferably a DNA adduct forming genotoxic compound.

In a further preferred embodiment, said characterizing step comprises determining the effect of said agent on expression of at least two, preferably, at least three DNA repair genes.

The invention also relates to a method as described above wherein the DNA repair genes are selected from the group consisting of POLR2D, RAD51, XRCC4, SMUG1, POLR2A, DDB2, MBD4, MAD2L2, ERCC1, ERCC3, REV3L and MGMT.

The invention also relates to a method as described above wherein samples are taken at more than one, preferably more than two predetermined time points.

In a further preferred embodiment of the method of this invention, said eukaryotic cell is a mammalian cell or even more preferably a human cell.

The term "DNA-interacting genotoxicity" refers to the genotoxicity of an agent resulting from the direct physical interaction of the agent with the DNA of a cell. Such direct physical interaction includes, for example, direct chemical and physical interactions and reactions with DNA molecules, intercalations with DNA molecules, the formation of adducts with the DNA molecules, the formation of intra-DNA molecule and inter-DNA molecule cross-linking and the formation of DNA-protein cross-linking.

The term "genotoxicity" means being characterized as causing damage to the genetic material of a live cell. The damage to the DNA or RNA of a cell may include, for example, damage resulting from nucleotide or polynucleotide deletion, addition, point mutation, dimerization or recombination, DNA-DNA, RNA-RNA and RNA-DNA cross-linking, DNA-protein or RNA-protein cross-linking and DNA or RNA breakage or degradation. The damage may also include that which is evidenced by chromosomal numerical abnormalities, such as polyploidy or aneuploidy.

The term "increase in expression" when used in reference to the expression of one or more genes, means expression that represents at least a biologically or otherwise significant increase as measured against a control.

The term "decrease in expression" when used in reference to the expression of one or more genes, means expression that represents at least a biologically or otherwise significant decrease as measured against a control.

DETAILED DESCRIPTION OF THE INVENTION

Chemicals can cause cancer through a variety of mechanisms. Genotoxic carcinogens lead to damage of the genetic material, either directly by covalently binding to DNA or indirectly by interfering with the mitotic machinery, ultimately leading to mutations in genes or large aberrations in chromosomes (1). If tumour suppressor genes are inactivated or proto-oncogenes are activated by this process, this may lead to cancer formation. The mode of action of non-genotoxic carcinogens can be very diverse, such as stimulation of cell proliferation, suppression of apoptosis, induction of oxidative stress, activation of biotransformation enzymes, suppression of the immune system, etc., but does not include damage to DNA or chromosomes (2).

Polycyclic aromatic hydrocarbons (PAH) comprise of a large group of structurally related compounds, including many carcinogens, to which humans are daily exposed through the environment and food. Many carcinogenic PAH, such as benzo[a]pyrene (BaP), share both genotoxic and non-genotoxic properties. During several enzymatic steps involving cytochrome P450 enzymes and epoxide hydroxylase, BaP is converted into the ultimate genotoxic carcinogen benzo[a]pyrene-7,8-dihydrodiol-9,10-epoxide (BPDE). BPDE can form DNA adducts, mainly BPDE-N2deoxyguanosin (BPDE-dG) (3). If not repaired, these adducts lead to mutations (4). BaP can also be transformed into radical cations (5) and reactive and redox-active o-quinones, which also can form DNA adducts (6, 7). Auto-oxidation of intermediates and/or redox cycling of o-quinones generates reactive oxygen species (ROS) capable of modifying DNA, leading to oxidised nucleotides like 8-hydroxy-deoxyguanosine (8-OHdG) (8). These processes all comprise the genotoxic properties of BaP.

The non-genotoxic properties of PAH are assumed to act through activating the transcription factor AhR, the aromatic hydrocarbon receptor, which thereupon dimerizes with the AhR nuclear translocator (ARNT). The AhR-ARNT complex binds to the dioxin-responsive elements (DRE) in the promoter regions of genes, thereby inducing their transcription (9). Many genes are involved in metabolism of carcinogens, including phase I enzymes like CYP1A1, CYP1A2 and CYP1B1 and several phase II enzymes (10).

In addition, PAH-mediated oxidative stress leads through the activation of transcription factor Nrf2 to the induction of multiple phase I and II biotransformation enzymes, including aldo-keto reductases, glutathione S-transferase-P, NAD(P)H: quinone oxireductases and UDP-glucuronosyl transferase 1A6 (11). Nrf2 protects against induction by BaP of DNA adducts, mutations and tumours in mice (12).

In order to protect the cells from the deleterious effects of DNA damage, several processes have developed. The cells can repair the damaged DNA by a many different mechanisms. In the case of BaP, the most relevant are nucleotide excision repair (NER) for the BPDE-DNA adducts and base excision repair (BER) for the oxidised damages (13, 14). In order to allow more time for repair, cell proliferation can be blocked at several phases of the cell cycle, such as at G1-S transition, S-phase and G2-M transition. In stead of going into cell cycle arrest, apoptosis can be induced, especially at high DNA damage levels (15).

Whereas exposure of cells to a full carcinogen like BaP is likely to induce multiple effects, their time dependencies and possible functional interactions are not well understood. Revealing successive waves of related gene expression changes linked with phenotypical markers can provide more insight into this. The objective of our study therefore is to investigate time-dependent changes in the cellular responses upon exposure to a full carcinogen, thereby using BaP as a model compound. This is achieved by extensive time series analyses of global gene expression changes in human hepatoma cells (HepG2) in relation to phenotypic events such as DNA adduct formation and cell cycle progression. HepG2 cells represent the liver as target organ for PAH-related carcinogenesis in vivo, are metabolically competent with respect to biotransformation of mutagens and carcinogens, are frequently used in toxicology and gene expression studies, and carry no p53 mutations (16-19).

Chemical carcinogens, and especially full carcinogens such as BaP which show both genotoxic as well as non-genotoxic properties, are known to be able to cause a multitude of effects in cells. These can range from altering the cellular metabolic capacity, to inducing DNA damage and repair, mutagenesis, and influencing cell growth and viability, and many others.

In our study, we show that a reliable analysis of the genotoxicity of a compound may be determined by studying the expression level of a limited number of genes under the influence of that compound. Hence, the invention relates to a method for the identification of genotoxic carcinogenic compounds wherein a eukaryotic cell is exposed to a potentially genotoxic compound in a culture medium whereafter samples are taken from the cell and/or the culture medium at least one predetermined time point which samples are then analysed for increased or decreased expression levels of at least three DNA repair genes as compared to a control cell that is not exposed to the carcinogenic compound. It was found that a combination of at least three different DNA repair genes provided unexpected improvements in sensitivity and/or specificity over the methods disclosed in the prior art.

Such DNA repair genes may advantageously be selected from the group consisting of POLR2D, RAD51, XRCC4, SMUG1, POLR2A, DDB2, MBD4, MAD2L2, ERCC1, ERCC3, REV3L, MGMT, FEN1, RFC2, POLD4, and CCNH. A skilled person will know which genes are depicted here by their Gene Symbol.

In a preferred embodiment, the genes are preferably selected from the group consisting of POLR2D, RAD51, XRCC4, SMUG1, POLR2A, DDB2, MBD4, MAD2L2, ERCC1, ERCC3, REV3L and MGMT.

Chemical carcinogens, and especially full carcinogens like BaP which show both genotoxic as well as non-genotoxic properties, cause a multitude of effects in cells. These range from altering the cellular metabolic capacity, to inducing DNA damage and repair, mutagenesis, and influencing cell growth and viability. As many of these processes are exerted through changing the expression of genes at the level of mRNA, genome-wide transcriptome profiling over an extensive period and multiple time points can provide detailed insight into these processes and their regulations and interdependencies.

In our study, transcriptome responses HepG2 cells were time-dependently compared to BaP exposure levels, DNA adduct levels, distribution of cells over various phases of the cell cycle and apoptosis. We show clear temporal functional changes and temporal profiles for a limited set of genes as disclosed above, demonstrating both early and late effects in up- and downregulation, and for clusters of correlating genes.

We delineated these gene expression changes in numerous alterations of biological pathways and processes, by several tools and approaches. Eventually, we identified by Reactome altered biological processes at the level of reactions and reaction pathways, and by T-profiler modulated biological pathways and processes.

What do all these changes teach us about the biological effects in these carcinogen-exposed cells? To understand that, we finally correlated changes in phenotypical and biological parameters (BaP levels in medium, BaP-DNA adducts, and various phases of the cell cycle) with those in reactions, pathways and gene sets by the time-series analyses tool STEM (Table 1).

Four and one pathways/processes [WAT IS DIT??] show a clear positive or negative correlation, respectively, with BaP levels in medium (Table 1). The correlation with TCDD responsive genes is as expected, since also PAHs like BaP activate AhR (9). Several cell cycle-related reaction pathways correlate with BaP levels, and thus are induced mainly during the first 36 h. Indeed in this period the largest transitions occur in cell cycle distributions, namely the drastic increase of S cells and decrease of G1 and M/G2 cells between 12 and 18 h. This suggests that at that moment, cells blocked in G1 or early S can go into S-phase. BaP is indeed known to induce the G1/S-phase arrest and also to block DNA synthesis at replication forks (26-29). A negative correlation of BaP is observed with the TGFβ signalling pathway, which is down regulated at early time points and thereafter upregulated. Genes in this pathway modulated by BaP are FURIN, SMAD2, SMAD3 and TGFBR2. Reduced levels of TGFR2 mRNA and protein occur in some human and mouse lung tumours, among others those induced by BaP (30).

BaP-DNA adducts and cells in S-phase cluster together and show a positive correlation with 10 pathways/processes/reactions (DNA repair related gene sets, many DNA damage and stress response related gene sets; Table 1), and with 2 a negative correlation (integration of energy metabolism, and chromosome organisation).

Figure 2:
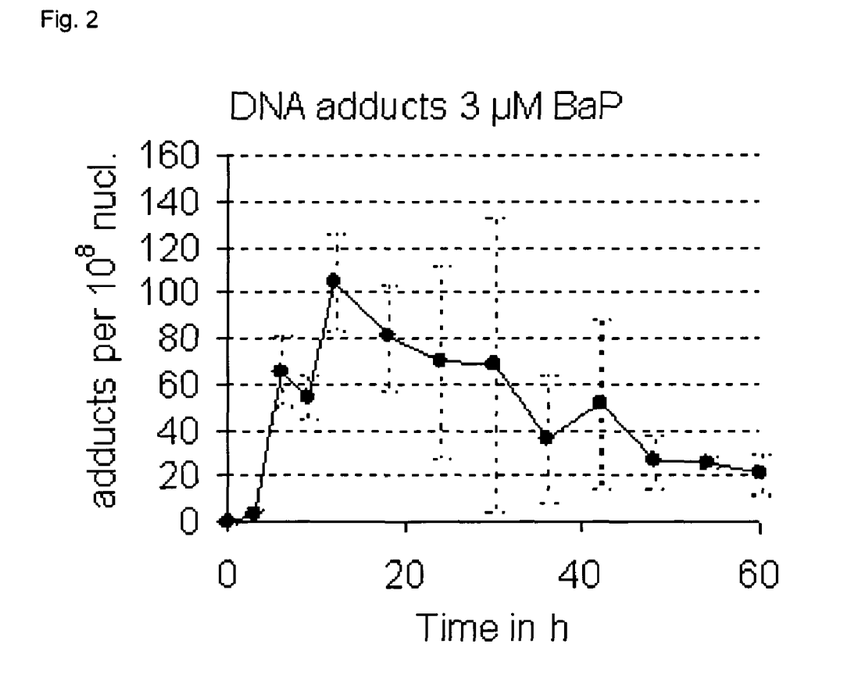
FIG. 2 Levels of BaP DNA adducts in HepG2 cells exposed to 3 micromolar BaP. Cells are analysed after various exposure times to 3 micromolar BaP; the mean and range of two independent experiments are indicated.

Most interesting are the effects on DNA repair pathways: both base excision reaper (BER) and global genomic repair (GC-NER) correlate with DNA adducts and are induced from 9/12 h until 60 h (FIG. 2). Reactive oxygen species (ROS) is expected to be formed during the metabolic activation of BaP. ROS leads to DNA damage, such as 8-OHdG, which is repaired by BER (14). Although at 30/36 h most BaP has been consumed, its metabolites and intermediates are still present and thus may cause an extended oxidative stress. Indeed, the induction of BER agrees very well with the period that the gene set "T-profiler_3—NRF2-regulated gene sets+motifs" is induced. Through the activation of transcription factor Nrf2, ROS induces the expression of many genes with antioxidant responsive elements in their promoter regions (11). The BER genes modulated by BaP are FEN1, MBD4, POLD4 and SMUG1, some of which are also affected by ultraviolet light (31).

Repair of bulky DNA damages—like BaP-DNA adducts—is by NER (13) and most of that is strand-specific: the transcribed strand is faster repaired than the non-transcribed strand (32, 33). This is well reflected by the gene expression alterations we observed: the TC-NER reaction pathway is upregulated for a shorter period then the GC-NER reaction pathway, namely from 9-42 and 9-60 h, respectively (FIG. 2). Five out of the eight NER genes modulated by BaP are in both GG-NER and TC-NER. DDB2 is specific for GG-NER and upregulated from 9-60 h; POLR2A and POLR2D are specific for TC-NER and upregulated at early time points or downregulated at late time points, respectively. Effects by BaP on DDB2 have been described before in MCF-7 cells but not in HepG2 cells (34, 35).

Taken together, our data suggest that the DNA damage repair system is regulated to some extent at the level of transcription. To our knowledge, this differential transcriptional regulation of various DNA damage repair pathways upon exposure to a genotoxic stressor, has not been described before. Till now, regulation of DNA damage repair pathways has been considered to occur mostly at post-translational level through protein modifications rather then gene expression (36, 37).

The correlation of BaP-DNA adducts with many pathways representing the DNA damage response, like "REACT_1059—extrinsic pathway for apoptosis", "T-profiler_2—P53 Upregulated genes+JUN motifs", and "T-profiler_4—many genotoxic stress related gene sets" is as expected, since PAHs like BaP cause genotoxic damage and induce the DNA damage response pathway (26, 28). Although many pathways/processes/reactions related to apoptosis are induced, BaP causes only a marginal induction of apoptosis at the doses used here. Apparently, the apoptotic machinery is activated, but BaP-induced damages are repaired sufficiently to halt that process before execution. At higher BaP doses and by other PAHs, apoptosis is induced in HepG2 cells (29). The set of genes identified by Hockley et al. to be affected by BaP in HepG2 cells (35), is part of "T-profiler_4—many genotoxic stress related gene sets". Furthermore, DNA adducts correlate with several stress related gene sets, such as "T-profiler_3—Nrf2-regulated gene sets+motifs" for ROS (discussed above), and for more general stress the gene sets "T-profiler_7—stress related?", T-profiler_15—many immune response related gene sets" and "React_6900—signaling in immune system". An overlap between immune response related gene sets and stress response may be through the p38 MAPK kinases (38).

Negative correlation of BaP-DNA adducts and cells in S-phase with integration of energy metabolism and chromosome organisation processes cannot be clearly understood.

Figure 1:
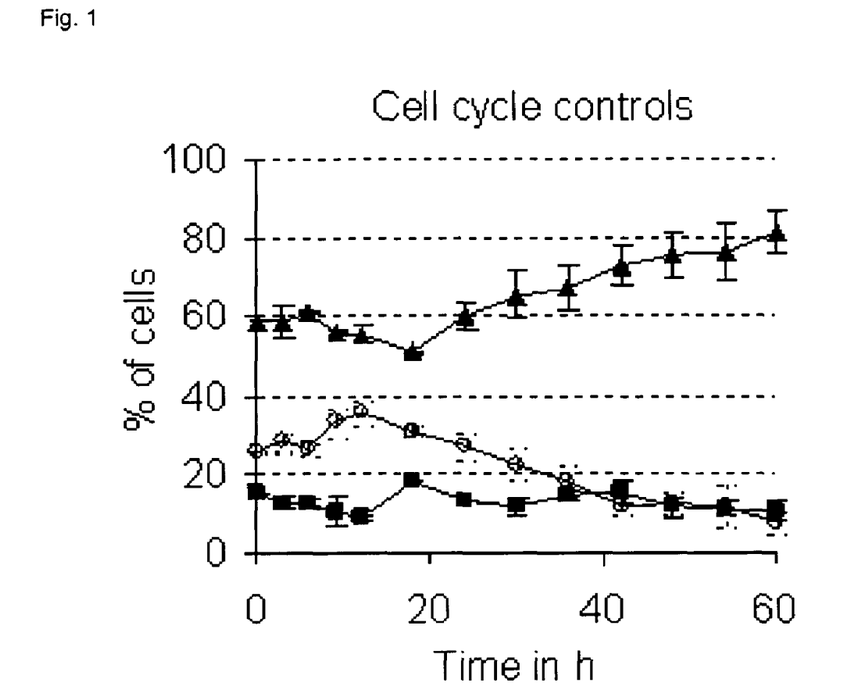
FIG. 1 Cell cycle distribution in control HepG2 cells. Cells are analysed after various times; the mean and range of two independent experiments are indicated.

Cells in G1-phase of the cell cycle are decreased from 18 to 24/36 h. G1-cell count shows a positive correlation with four pathways/processes/reactions and a negative correlation with 14 others. Many of these were also found to correlate with DNA adducts and cells in S-phase, but then in the reverse direction, confirming that G1-cell count and DNA adduct levels are inversely related (FIG. 1). A positive correlation of G1-cells with "React_13—metabolism of amino acids", "React_1505—integration of energy metabolism", "T-profiler_8—metabolism of amines, sterol, cholesterol" and "T-profiler_9—chromosome organisation" corresponds with the downregulation of these pathways/processes from ca 18 to 36 h. In fact, many gene sets for metabolic processes of amino acids, lipids, and steroids and downregulated from 12/18 h until 36/42 h, whereas those for nucleotides are upregulated. This suggests that in the period when DNA adduct levels are high and G1-cell levels are low, the metabolism of the cells is mainly directed towards that of nucleotides—possibly indicating the increased demand for nucleotides during the excision repair of DNA adducts—, while for other cellular compounds like amino acids and lipids, metabolism is turned low. Once cell cycle distribution is back to normal and adducts have mostly been repaired, metabolic processes return to their normal levels. Indeed, "React_1698—nucleotide metabolism" shows a negative correlation with G1-cells (Table 1). Besides with the gene sets positively correlating with DNA adduct levels, G-cells also negative correlate with several another gene sets representing the DNA damage response, namely "React_964—intrinsic pathway for apoptosis". Interestingly, the G-cells show a negative correlation with "React_1590—G1 phase", indicating that upregulation of this reaction pathway does not necessarily agree with the actual cell cycle phase.

Cells in S-phase show a short but drastic increase from 18 to ca 30 h, with a concomitant decrease of cells in G1 and G2 phases (FIG. 1). This suggests an arrest of cells in S-phase and/or a stimulation of G1-cells to go into S-phase. Kinetic analyses of progression of cells into various phases of the cell cycle at various time points after BaP exposure are required to clarify this further. Only 1 gene set correlates with levels of S-phase cells, namely "React_2188—ribonucleotide salvage", which agrees with the need of cells in S-phase for synthesis of nucleotides. Other reactions related to nucleotide synthesis are also induced, but they correlate better with DNA adducts, and have been discussed above.

Ten pathways/processes/reactions have been shown to correlate with G2/M-cells, which are increased from ca 24/36 to 54 h (FIG. 1). The positive correlation is with diverse groups of genes sets, such as metabolism of carbohydrates, lipids and lipoproteins, execution of apoptosis, mitotic spindle execution, protein degradation, etc. Noteworthy, the negative correlation is mainly with reactions involved in gene expression, transcription and translation. Most of these show an initial upregulation followed by a downregulation thereafter. An order is apparent: the induction period increases from 6 h for "React_11052—metabolism of non-coding RNA" (such as miRNAs), 15 h for "React_1675—mRNA processing", 27 h for "React_1014—translation" and 39 h for "React_1788—transcription" (see FIG. 2). This suggests that the regulation of these reaction pathways is strictly organised.

Our data point out that a full carcinogenic compound like BaP, with a genotoxic component through the induction of DNA adducts and mutations and a non-genotoxic component via the AhR transcription factor, may also influence many other reactions/pathways that affect the carcinogenic process. Examples are the various DNA repair processes (BER, TC-NER and GG-NER), gene expression process (e.g. metabolism of non-coding RNA, which includes miRNAs), and many signalling pathways (see FIG. 2). The factual relevance of these modulations for cancer formation is not clear yet, which thus represents a challenge for future investigations to further unravel the chemical carcinogenesis process.

Effects of BaP on gene expression changes as measured by DNA microarrays in HepG2 cells have been published before, but on maximally 4 time points (19, 29, 35, 39). This study, however, is the first with so many time points in a toxicogenomic evaluation of a chemical carcinogen. Therefore, our data set may serve as benchmark for others, in order to compare with responses induced by other carcinogenic compounds or in other cells or organisms, to develop new bioinformatic tools for time-series analyses, functional annotation and correlation analyses of transcriptome sets with phenotypic parameters, etc.

In the current detailed time series study, numerous temporal changes in clusters of genes upon exposure of cells to the carcinogen BaP have been observed, thereby providing an unprecedented insight in time-dependent interactions of the affected processes and pathways. TCDD responsive genes, many of them regulated through AhR, are those showing the earliest effect. Most interesting are the slower effects, however, such as on DNA repair. Transcription-coupled nucleotide excision repair lasts ca 18 h, until ±50% of the DNA adducts have been repaired, whereas global genomic nucleotide excision repair and base excision repair is upregulated up to 60 h, at which time point adducts are still present. The data also suggest that when G1-cell levels are low and DNA adduct levels are high, the metabolism of nucleotides is high, while that for amino acids and lipids is low. Once cell cycle distribution has returned to normal and most adducts are repaired, metabolic processes also return to normal levels. Also noteworthy are the sequential periods during which several reaction pathways in gene expression, transcription and translation are upregulated. All observations indicate that the cellular transcriptome is strictly regulated, with main responses once DNA damages are generated, and adapts to the changing needs of cells following acute exposure to a carcinogen.

TABLE 1

Summary of the correlation analyses between biological parameters and pathways, processes, gene sets from the functional annotation tools T-profiler and Reactome (the data from FIG. 2 and 3) as given by the time-series analysis tool STEM.

Positive correlation with BaP levels

React_899 - S phase
React_1725 - M/G1 transition
React_2254 - G1/S DNA damage checkpoints
T-profiler_5 - TCDD responsive genes
Negative correlation with BaP levels React_6844 - signaling by TGF beta
Positive correlation with adduct levels S cells
React_1059 - extrinsic pathway for apoptosis
React_1104 - base excision repair
React_2253 - global genomic NER (GG-NER)
React_6900 - signaling in immune system
T-profiler_1 -
T-profiler_2 - p53 up-regulated genes + JUN motifs
T-profiler_3 - Nrf2-regulated gene sets + motifs
T-profiler_4 - many genotoxic stress related gene sets
T-profiler_7 - stress related?
T-profiler_15 - many immune response related gene sets
Negative correlation with adduct levels S cells
React_1505 - integration of energy metabolism
T-profiler_9 - chromosome organisation
Positive correlation with G1 cells React_13 - metabolism of amino acids
React_1505 - integration of energy metabolism
T-profiler_8 - metabolism of amines, sterol, cholesterol
T-profiler_9 - chromosome organisation
Negative correlation with G1 cells React_964 - intrinsic pathway for apoptosis
React_1059 - extrinsic pathway for apoptosis
React_1104 - base excision repair
React_1590 - G1 phase
React_1698 - nucleotide metabolism
React_2253 - global genomic NER (GG-NER)
React_6900 - signaling in immune system
React_11061 - signalling by NGF
T-profiler_1 -
T-profiler_2 - p53 up-regulated genes + JUN motifs
T-profiler_3 - Nrf2-regulated gene sets + motifs
T-profiler_4 - many genotoxic stress related gene sets
T-profiler_7 - stress related?
T-profiler_15 - many immune response related gene sets
Positive correlation with S cells Same as for adduct levels
Negative correlation with S cells Same as for adduct levels
Positive correlation with G2/M cells React_474 - metabolism of carbohydrates
React_602 - lipid and lipoprotein metabolism TABLE 1-continued Summary of the correlation analyses between biological parameters and pathways, processes, gene sets from the functional annotation tools T-profiler and Reactome (the data from FIG. 2 and 3) as given by the time-series analysis tool STEM.

React_995 - apoptotic execution phase
React_2137 - mitotic spindle checkpoint
React_6828 - APC/C-mediated degradation of cell cycle proteins
React_11044 - signaling by Rho GTPases
T-profiler_10 - nucleosome organisation
T-profiler_12 - GTPase-regulated gene sets
T-profiler_13 -
T-profiler_14 - diverse (membrane, extracellular region, endopeptidase)
Negative correlation with G2/M cells React_71 - gene expression
React_1014 - translation
React_1628 - transcription-coupled NER (TC-NER)
React_1675 - mRNA processing
React_1788 - transcription
React_9417 - signaling by EGFR
React_11052 - metabolism of non-coding RNA
T-profiler_6 - RNA metabolism and processing, regulation of transcription

EXAMPLES

Example 1

Cell Culture and Treatment

HepG2 cells were cultured and treated with 3 µM BaP (purity 97%, CAS no. 50-32-8; Sigma-Aldich, Zwijndrecht, the Netherlands) or vehicle control (DMSO, 0.1%) as described previously. This is the lowest BaP dose with a maximum accumulation of cells in S-phase (29). The cells were exposed for 3 to 60 h where after they were either fixed with cold methanol and stored at −20° C. for FACS analysis or media was removed from the culture flasks and Trizol (Gibco/BRL, Breda, The Netherlands) was added for RNA and DNA isolation. Two independent experiments were conducted.

Example 2

BaP in Culture Medium

BaP levels in culture medium were determined following extraction with hexane, evaporation of hexane, dissolving the residue in acetonitrile, and analyses on an HPLC gradient system (Supelcosil LC-PAH [column 25 cm*4.6 mm, 5 um]; solvent gradient at 1.5 ml/min: 3 min 64% Acetonitril—a linear gradient to 100% acetonitril in 20 minutes—a 15 min hold at this) with fluorescence detection (ex/em at 280/>350 nm).

Example 3 yH2AX Foci Analysis

HepG2 cells cultured and exposed on cover slils were analysed for DNA double strand breaks by immunofluorescence staining of yH2AX foci as described (42). Following fixation, foci were stained with the anti-phospho-Histone H2A-X (ser139) Clone JBW 301 antibody (Upstate Biotechnology, Lake Placid, N.Y.) and Alexa fluor 488 goat anti-mouse IgG antibody (Invitrogen, Breda, The Netherlands). Cells were scored manually using a damage score, ranging from 0 to 4, and sample scores (100 cells/sample) are given as percentage of the maximal damage.

Example 4

Flow Cytometric Analyses for Cell Cycle and Apoptosis

Analyses of cell cycle profiles and apoptosis was performed as previously described using a FACSort (Becton Dickinson, Sunnyvale, USA) (29). For DNA content cells were stained with propidium iodide; apoptotic cells were visualised with the primary antibody M30 CytoDeath (Roche, Penzberg, Germany) and FITC conjugated anti-mouse Ig as secondary antibody (DakoCytomation, Glostrup, Denmark). For each sample 10,000 cells were analyzed. Cells in the G0-1, S or G2-M phase were expressed as a percentage of the total number of cells.

Example 5

RNA and DNA Isolation

RNA was isolated from the Trizol solutions according to the producer's manual and purified with the RNeasy mini kit (Qiagen Westburg bv., Leusden, The Netherlands). After isolation, the remaining phases were used for DNA isolation according to manufacturer's protocol. RNA and DNA quantity was measured on a spectrophotometer and RNA quality was determined on a BioAnalyzer (Agilent Technologies, Breda, The Netherlands). Only RNA samples which showed clear 18S and 28S peaks and with a RIN level higher than 8 were used.

Example 6

DNA Adduct Analyses

DNA adduct levels were determined by 32P-postlabelling according to the procedure originally described by Reddy and Randerath (43) with modifications described by Godschalk et al (44).

Example 7

Gene Expression Analyses with DNA Microarrays

Labelling and Hybridization

Labelling and hybridisation of RNA samples was done according to Agilent's manual for microarrays (Agilent Technologies, Breda, The Netherlands). Samples from BaP or vehicle treated cells was labelled with Cyanine 3 (Cy3) or Cyanine 5 (Cy5). cRNA of the time-matched treated and control samples was applied on the G4110B Agilent 22K Human Oligo Microarray, hybridized and washed according to Agilent's manual and slides were scanned on a ScanArrayExpress (Packard Biochip Technologies, Perkin Elmer life sciences, Boston, USA) with fixed laser power (100%) and PMT gain (55% for Cy5 and 60% for Cy3). For each biological experiment, two hybridizations per time point were conducted, with swapped Cy3 and Cy5 dyes. In total this resulted in 48 hybridisations.

Image Analysis and Processing

The images (10 micron resolution; 16 bit tiff) were processed with ImaGene 6.0 to quantify spot signals (BioDiscovery Inc., Los Angeles, USA). Irregular spots were automatically flagged and excluded from data analysis. Data from ImaGene were further processed with GeneSight 4.1.6 (BioDiscovery Inc., Los Angeles, USA). For each spot, background was subtracted and flagged spots as well as spots with a net expression level below 20 in both channels were omitted. Data were log base 2 transformed and LOWESS normalized. If for a gene more probes were on the array, replicates were averaged while omitting outliers (>2 standard deviations). Raw data are available at ArrayExpress (accession numbers E-TOXM-22 and E-TOXM-23, for the first and second experiment respectively) (www.ebi.ac.uk/arrayexpress/).

Example 8

Gene Expression Data Analyses and Data Mining

Differentially Expressed Genes

First genes were selected for which all four replicate hybridizations gave an expression difference of >0.2 or all four ←−0.2 (meaning all replicates in the same direction; on a normal scale, this is a 15% increase or decrease of transcript level). This resulted in 5211 genes. Second, genes were selected by ANOVA using the plug-in "Time series analysis" from BRB Array Tools (version 3.4 and R version 2.2.0; linus.nci.nih.gov/BRB-ArrayTools.html) with "Time" as descriptor. This resulted in 2808 genes with a False Discovery Rate (FRD)<0.1. All further analyses on significantly differentially expressed genes, start with these 2808 genes.

Time Series Analyses

For identification of genes, reactions, pathways or gene-sets co-regulated time-dependently and correlating with a biological parameter, the software tool "Short Time-series Expression Miner" (STEM, version 1.1.2b; www.cs.cm-u.eduhjernst/stem/) was used (24, 25). STEM finds statistically significant patterns from time series microarray experiments and can compare data sets across experiments. The clustering algorithm assigns each gene, reaction, pathway or gene-set to these profiles based on correlation coefficients (>0.6) and permutation analyses (n=50). For all parameters, log-transformed data were used, normalised such that treated-control ratios ranged from +1 to −1, with 0 for no change.

Functional Interpretation of Significantly Differentially Expressed Gene sets

Reactome (www.reactome.org; Version 25, August 2008) (45) is used to examine the biological processes that may be affected at the level of reactions and reaction pathways, a level of detail that cannot be obtained by gene ontology annotations, and KEGG and BioCarta pathways. Reactions are grouped into causal chains to form pathways. The tool Skypainter is used to determine per time point which events (reactions and/or reaction pathways) harbour differentially expressed genes (down- and upregulated genes separately), selecting only events with at least 3 genes. The ratio of these number of differentially genes per event with total numbers present in the set of 2808 genes, are used for visualisation of affected pathways. Rctions were ordered by main pathway and sub-pathway.

Functional Interpretation of All Expressed Genes

T-profiler is used for functional annotation of pathways and processes in the complete data set of genes without pre-selecting modulated genes. T-profiler uses the unpaired t-test to score the difference between the mean expression level of predefined sets of genes and that of all other genes within the complete data set (46). Pathways and processes included gene sets from GO terms, KEGG pathways, GenMAPP pathways, BioCarta pathways, Motifs, Broad/MIT pathways, (manually curated) gene sets and gene sets retrieved from literature, i.e. lists of genes modulated by BaP or TCDD in HepG2 cells (35, 47, 48) and a set of genes with known antioxidant response elements (AREs), also known as Nrf2 binding sites (11). Per experiment and time point t-values were determined for each gene set. Only gene sets with an absolute t-value>4 at at least 2 succeeding time points in both experiments were selected for further analyses.

Example 9

Effects on BaP Levels, DNA Adduct Levels, Cell Cycle and Apoptosis

Clearance by HepG2 cells of BaP from the culture medium was fast, with 1% remaining after 30-36 h, levels being not detectable after 48 h (see FIG. 1 of the Supporting Information). BaP-DNA adduct levels increased between 3-6/12 h, were stable until 18/30 h, where after they slowly declined (FIG. 1). Adduct levels stabilise to 15-25% of the highest level, even after 60 h, suggesting a diminished repair of adducts during the last 12-30 h. Similar results were obtained by in situ staining for yH2AX foci, a marker for double strand DNA breaks (20). At 9 h this was induced, at 24 h it was maximal, and at 48 h it was decreased to ca. 25% (FIG. 2 of the Supporting Information). Analyses of cell cycle distributions, shows that at 18 h BaP causes a drastic increase in S-phase cells with a concomitant decrease of cells in G1 and G2 phases (FIG. 1). This S-phase accumulation lasts 6-18 h, where after the number of S-phase cells decrease with a concomitant increase of G2/M-phase cells. After about 54 h, the distribution of BaP-treated cells becomes similar to that of the controls. In the control cultures, the % of cells in S-phase increase after 18-24 h together with a decrease of G1-phase cells. This is probably due to depletion of the culture medium for essential compounds. Apoptotic cells levels did not increase due to BaP treatment, varied between 0.5-3% for control and BaP cultures, and were slightly higher in the first experiment (data not shown).

Example 10

Effects on Gene Expression

Differentially Expressed Genes

Figure 3:
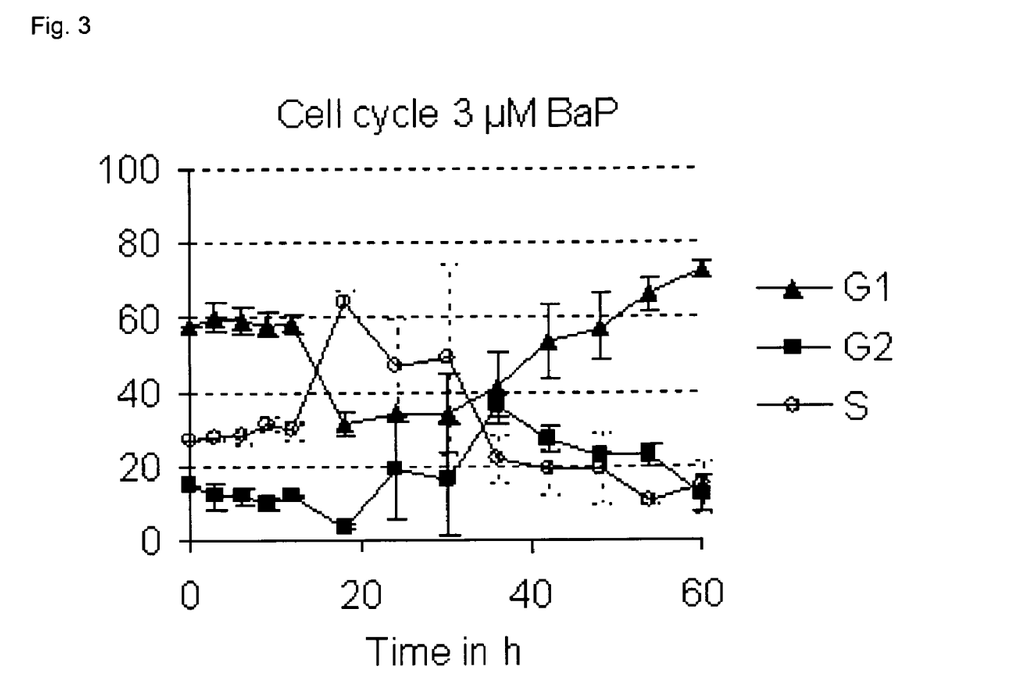
FIG. 3 Cell cycle distribution in HepG2 cells exposed to 3 micromolar BaP. Cells are analysed after various exposure times to 3 micromolar BaP; the mean and range of two independent experiments are indicated.

Gene expression profiles were determined by DNA microarrays, resulted in 48 hybridisations, 4 per time point. Differentially expressed genes were identified by reproducible similar changes over the 4 replicates, combined with ANOVA, resulting in 2808 differentially expressed genes. The same approach on randomised arrays resulted in not one significantly affected gene, which indicates that few false-positives were obtained. Visualisation of the log base 2 expression ratios for these 2808 genes and all arrays in a heat map, shows a high reproducibility in the expression profiles between the various replicate experiments and arrays (FIG. 3 of the Supporting Information).

Pathway Analyses by Reactome

In order to examine the responses that may occur at the level of reactions and reaction pathways, the sets of differentially expressed genes per time point were analysed in Reactome. An overview of the affected reaction/pathways is in FIG. 2 (Supporting Information excel file "Reactome data" for all data and other information, including reaction IDs), thereby focusing on reaction pathways/processes that are considered most relevant for chemical carcinogenesis. Over representation analyses based on functional annotation from GO-terms and other gene-sets was also done using FatiGO+ (babelomics.bioinfo.cipf.es) (21), but results were limited and thus are not presented.

Pathway Analyses by T-Profiler

T-profiler was used to identify affected functions using the complete data set, thus without pre-selecting modulated genes. Besides gene sets based on GO annotation etc, also gene sets retrieved from literature were incorporated. Following an analysis per time point, in total 155 gene sets were identified as being modulated (Supporting Information excel file "T-profiler data"). Hierarchical clustering of these sets was used to group these gene sets (FIG. 3). The main functional annotations of these clusters show upregulation of TP53, JUN and NRF2 signalling pathways, and responses induced by genotoxic stressors. Downregulation consists of metabolisms of amines, sterols and cholesterol, transcription and RNA processing, nucleosome assembly and GTPase regulation. These confirm the Reactome data, though provide less in-depth information but more statistical evaluation.

Time-Related Effects of the Functional Data

Numerous different approaches can be used to identify co-regulated genes with time-related patterns in time series experiments on microarray studies, including hierarchical clustering, or dedicated tools such as CAGED (22), GQL (23) and STEM (24, 25). All these tools have been applied on our gene expression data set. Although STEM resulted into the most comprehensible information, this mainly confirmed the data from the functional annotation analyses mentioned above and thus is not presented here.

STEM was also used to uncover time-related patterns in the reactions, pathways and biological processes as identified by Reactome and T-profiler (FIGS. 2 and 3), in combination with the phenotypical parameters (BaP levels in medium, BaP-DNA adducts, and various phases of the cell cycle). Both positive and negative correlations are summarised in Table 1 (Supporting Information Excel file "STEM data of pathways and processes" for more detailed information) and further discussed below.

Example 11

Correlation Analysis

The gene expression data from the HepG2 time series of DNA repair genes obtained with the Agilent assays were compared with the gene expression on Affymetrix chips. Two genotoxic compounds were measured in a method according to the invention as well as 5 non-genotoxic compounds. Measurements were performed at three different time points; 12, 24 and 48 hours. Table 2 shows a correlation analysis for differential gene expression between the aggilent assays and the Affymetrix chips.

Genes 1 to 9 appeared to have the best correlation between both assays for genotoxic compounds. Genes 10 to 12 had a good correlation for BaP but less for AfN1. As a control, genes 13 to 16 are shown that were found to have a bad correlation for both genotoxic compounds. Note that the correlation for non-genotoxic compounds is low in all cases.

TABLE 2 correlation analysis.

| Gene number | Agilent Gene Symbol | GTX BaP-Aff | GTX AFB1 | NGTX TCDD | NGTX CsA | NGTX ampc | NGTX DMSO | NGTX Estradiol | GTX all | NGTX all |
|---|---|---|---|---|---|---|---|---|---|---|
| 1 | POLR2D | 0.95 | 0.95 | 0.44 | −0.24 | 0.87 | −0.12 | −0.06 | 0.95 | 0.18 |
| 2 | RAD51 | 0.88 | 1.00 | 1.00 | −0.51 | 0.13 | −0.86 | 0.27 | 0.94 | 0.01 |
| 3 | XRCC4 | 0.91 | 0.91 | 0.99 | 0.12 | 0.06 | 0.90 | −1.00 | 0.91 | 0.21 |
| 4 | SMUG1 | 0.91 | 0.89 | 0.73 | 0.99 | −0.74 | 0.56 | −0.94 | 0.90 | 0.12 |
| 5 | POLR2A | 0.98 | 0.79 | 1.00 | −0.42 | 0.85 | −0.47 | −0.87 | 0.89 | 0.02 |
| 6 | DDB2 | 0.87 | 0.89 | 0.55 | 0.29 | −0.01 | −0.27 | 0.14 | 0.88 | 0.14 |
| 7 | MBD4 | 0.93 | 0.78 | −0.32 | 0.31 | 0.42 | 0.44 | −0.82 | 0.86 | 0.01 |
| 8 | MAD2L2 | 0.97 | 0.53 | 0.25 | −0.10 | 0.99 | 0.17 | 0.14 | 0.75 | 0.29 |
| 9 | ERCC1 | 0.99 | 0.41 | −0.48 | 0.71 | −0.11 | −0.17 | −0.84 | 0.70 | −0.18 |
| 10 | ERCC3 | 0.99 | 0.03 | −0.35 | −0.61 | −0.55 | 0.32 | 0.94 | 0.51 | −0.05 |
| 11 | REV3L | 0.80 | −0.73 | 0.20 | 0.78 | −0.55 | 0.75 | −0.96 | 0.04 | 0.04 |
| 12 | MGMT | 0.98 | −0.97 | 0.70 | −0.52 | −0.23 | −0.93 | 0.23 | 0.00 | −0.15 |
| 13 | FEN1 | 0.45 | −0.33 | −0.50 | 0.75 | 1.00 | −0.71 | −0.12 | 0.06 | 0.08 |
| 14 | RFC2 | 0.43 | 0.07 | −0.02 | 0.57 | 0.97 | 0.11 | 0.40 | 0.25 | 0.41 |
| 15 | POLD4 | 0.42 | 0.44 | 0.53 | 0.72 | −1.00 | −0.66 | −0.53 | 0.43 | −0.19 |
| 16 | CCNH | 0.17 | 0.45 | 0.98 | 0.83 | −0.39 | −0.63 | −0.16 | 0.31 | 0.13 |

REFERENCES

1. Hayashi, Y. Overview of genotoxic carcinogens and non-genotoxic carcinogens. Exp Toxicol Pathol, 44: 465-471, 1992.
2. Shaw, I. C. and Jones, H. B. Mechanisms of non-genotoxic carcinogenesis. Trends Pharmacol Sci, 15: 89-93, 1994.
3. Cheng, S. C., Hilton, B. D., Roman, J. M., and Dipple, A. DNA adducts from carcinogenic and noncarcinogenic enantiomers of benzo[a]pyrene dihydrodiol epoxide. Chem Res Toxicol, 2: 334-340, 1989.
4. Moriya, M., Spiegel, S., Fernandes, A., Amin, S., Liu, T., Geacintov, N., and Grollman, A. P. Fidelity of translesional synthesis past benzo[a]pyrene diol epoxide-2'-deoxyguanosine DNA adducts: marked effects of host cell, sequence context, and chirality. Biochemistry, 35: 16646-16651, 1996.
5. Cavalieri, E. L. and Rogan, E. G. Central role of radical cations in metabolic activation of polycyclic aromatic hydrocarbons. Xenobiotica, 25: 677-688, 1995.
6. Penning, T. M., Burczynski, M. E., Hung, C. F., McCoull, K. D., Palackal, N. T., and Tsuruda, L. S. Dihydrodiol dehydrogenases and polycyclic aromatic hydrocarbon activation: generation of reactive and redox active o-quinones. Chem Res Toxicol, 12: 1-18, 1999.
7. Balu, N., Padgett, W. T., Lambert, G. R., Swank, A. E., Richard, A. M., and Nesnow, S. Identification and characterization of novel stable deoxyguanosine and deoxyadenosine adducts of benzo[a]pyrene-7,8-quinone from reactions at physiological pH. Chem Res Toxicol, 17: 827-838, 2004.
8. Caino, M. C., Oliva, J. L., Jiang, H., Penning, T. M., and Kazanietz, M. G. Benzo[a]pyrene-7,8-dihydrodiol promotes checkpoint activation and G2/M arrest in human bronchoalveolar carcinoma H358 cells. Mol Pharmacol, 71: 744-750, 2007.
9. Ma, Q. Induction of CYP1A1. The AhR/DRE paradigm: transcription, receptor regulation, and expanding biological roles. Curr Drug Metab, 2: 149-164, 2001.
10. Nebert, D. W., Dalton, T. P., Okey, A. B., and Gonzalez, F. J. Role of aryl hydrocarbon receptor-mediated induction of the CYP1 enzymes in environmental toxicity and cancer. J Biol Chem, 279: 23847-23850, 2004.
11. Wang, X., Tomso, D. J., Chorley, B. N., Cho, H. Y., Cheung, V. G., Kleeberger, S. R., and Bell, D. A. Identification of polymorphic antioxidant response elements in the human genome. Hum Mol Genet, 16: 1188-1200, 2007.
12. Aoki, Y., Hashimoto, A. H., Amanuma, K., Matsumoto, M., Hiyoshi, K., Takano, H., Masumura, K., Itoh, K., Nohmi, T., and Yamamoto, M. Enhanced spontaneous and benzo(a)pyrene-induced mutations in the lung of Nrf2-deficient gpt delta mice. Cancer Res, 67: 5643-5648, 2007.
13. Braithwaite, E., Wu, X., and Wang, Z. Repair of DNA lesions induced by polycyclic aromatic hydrocarbons in human cell-free extracts: involvement of two excision repair mechanisms in vitro. Carcinogenesis, 19: 1239-1246, 1998.
14. Izumi, T., Wiederhold, L. R., Roy, G., Roy, R., Jaiswal, A., Bhakat, K. K., Mitra, S., and Hazra, T. K. Mammalian DNA base excision repair proteins: their interactions and role in repair of oxidative DNA damage. Toxicology, 193: 43-65, 2003.
15. Bartek, J. and Lukas, J. DNA damage checkpoints: from initiation to recovery or adaptation. Curr Opin Cell Biol, 19: 238-245, 2007.
16. Knasmuller, S., Parzefall, W., Sanyal, R., Ecker, S., Schwab, C., Uhl, M., Mersch Sundermann, V., Williamson, G., Hietsch, G., Langer, T., Darroudi, F., and Natarajan, A. T. Use of metabolically competent human hepatoma cells for the detection of mutagens and antimutagens. Mutation research, 402: 185-202, 1998.
17. Wilkening, S., Stahl, F., and Bader, A. Comparison of primary human hepatocytes and hepatoma cell line Hepg2 with regard to their biotransformation properties. Drug Metab Dispos, 31: 1035-1042, 2003.
18. Hsu, I. C., Tokiwa, T., Bennett, W., Metcalf, R. A., Welsh, J. A., Sun, T., and Harris, C. C. p53 gene mutation and integrated hepatitis B viral DNA sequences in human liver cancer cell lines. Carcinogenesis, 14: 987-992, 1993.
19. Staal, Y. C., van Herwijnen, M. H., van Schooten, F. J., and van Delft, J. H. Modulation of gene expression and DNA adduct formation in HepG2 cells by polycyclic aromatic hydrocarbons with different carcinogenic potencies. Carcinogenesis, 27: 646-655, 2006.
20. Zhou, C., Li, Z., Diao, H., Yu, Y., Zhu, W., Dai, Y., Chen, F. F., and Yang, J. DNA damage evaluated by gammaH2AX foci formation by a selective group of chemical/physical stressors. Mutat Res, 604: 8-18, 2006.
21. Al-Shahrour, F., Minguez, P., Vaquerizas, J. M., Conde, L., and Dopazo, J. BABELOMICS: a suite of web tools for functional annotation and analysis of groups of genes in high-throughput experiments. Nucleic Acids Res, 33: W460-464, 2005.

22. Ramoni, M. F., Sebastiani, P., and Kohane, I. S. Cluster analysis of gene expression dynamics. Proc Natl Acad Sci USA, 99: 9121-9126, 2002.
23. Costa, I. G., Schonhuth, A., and Schliep, A. The Graphical Query Language: a tool for analysis of gene expression time-courses. Bioinformatics, 21: 2544-2545, 2005.
24. Ernst, J. and Bar-Joseph, Z. STEM: a tool for the analysis of short time series gene expression data. BMC Bioinformatics, 7: 191, 2006.
25. Bar-Joseph, Z., Siegfried, Z., Brandeis, M., Brors, B., Lu, Y., Eils, R., Dynlacht, B. D., and Simon, I. Genome-wide transcriptional analysis of the human cell cycle identifies genes differentially regulated in normal and cancer cells. Proc Natl Acad Sci USA, 105: 955-960, 2008.
26. Jeffy, B. D., Chen, E. J., Gudas, J. M., and Romagnolo, D. F. Disruption of cell cycle kinetics by benzo[a]pyrene: inverse expression patterns of BRCA-1 and p53 in MCF-7 cells arrested in S and G2. Neoplasia, 2: 460-470, 2000.
27. Bi, X., Slater, D. M., Ohmori, H., and Vaziri, C. DNA polymerase kappa is specifically required for recovery from the benzo[a]pyrene-dihydrodiol epoxide (BPDE)-induced S-phase checkpoint. J Biol Chem, 280: 22343-22355, 2005.
28. Hockley, S. L., Arlt, V. M., Jahnke, G., Hartwig, A., Giddings, I., and Phillips, D. H. Identification through microarray gene expression analysis of cellular responses to benzo(a)pyrene and its diol-epoxide that are dependent or independent of p53. Carcinogenesis, 29: 202-210, 2008.
29. Staal, Y. C., Hebels, D. G., van Herwijnen, M. H., Gottschalk, R. W., van Schooten, F. J., and van Delft, J. H. Binary PAH mixtures cause additive or antagonistic effects on gene expression but synergistic effects on DNA adduct formation. Carcinogenesis, 28: 2632-2640, 2007.
30. Kang, Y., Prentice, M. A., Mariano, J. M., Davarya, S., Linnoila, R. I., Moody, T. W., Wakefield, L. M., and Jakowlew, S. B. Transforming growth factor-beta 1 and its receptors in human lung cancer and mouse lung carcinogenesis. Exp Lung Res, 26: 685-707, 2000.
31. Garinis, G. A., Mitchell, J. R., Moorhouse, M. J., Hanada, K., de Waard, H., Vandeputte, D., Jans, J., Brand, K., Smid, M., van der Spek, P. J., Hoeijmakers, J. H., Kanaar, R., and van der Horst, G. T. Transcriptome analysis reveals cyclobutane pyrimidine dimers as a major source of UV-induced DNA breaks. Embo J, 24: 3952-3962, 2005.
32. Dreij, K., Seidel, A., and Jernstrom, B. Differential removal of DNA adducts derived from anti-diol epoxides of dibenzo[a,l]pyrene and benzo[a]pyrene in human cells. Chem Res Toxicol, 18: 655-664, 2005.
33. Mellon, I. Transcription-coupled repair: a complex affair. Mutat Res, 577: 155-161, 2005.
34. Mahadevan, B., Keshava, C., Musafia-Jeknic, T., Pecaj, A., Weston, A., and Baird, W. M. Altered gene expression patterns in MCF-7 cells induced by the urban dust particulate complex mixture standard reference material 1649a. Cancer Res, 65: 1251-1258, 2005.
35. Hockley, S. L., Mt, V. M., Brewer, D., Giddings, I., and Phillips, D. H. Time- and concentration-dependent changes in gene expression induced by benzo(a)pyrene in two human cell lines, MCF-7 and HepG2. BMC Genomics, 7: 260, 2006.
36. Branzei, D. and Foiani, M. Regulation of DNA repair throughout the cell cycle. Nat Rev Mol Cell Biol, 9: 297-308, 2008.
37. Huang, T. T. and D'Andrea, A. D. Regulation of DNA repair by ubiquitylation. Nat Rev Mol Cell Biol, 7: 323-334, 2006.
38. Chen, Y., Miao, Z. H., and Ding, J. [The emergent role of p38 MAPKs in the regulation of cell cycle]. Sheng Li Ke Xue Jin Zhan, 35: 315-320, 2004.
39. Hockley, S. L., Arlt, V. M., Brewer, D., Te Poele, R., Workman, P., Giddings, I., and Phillips, D. H. AHR- and DNA-damage-mediated gene expression responses induced by benzo(a)pyrene in human cell lines. Chem Res Toxicol, 20: 1797-1810, 2007.
40. Clarke, C. J. and Haselden, J. N. Metabolic profiling as a tool for understanding mechanisms of toxicity. Toxicol Pathol, 36: 140-147, 2008.
41. Merrick, B. A. and Bruno, M. E. Genomic and proteomic profiling for biomarkers and signature profiles of toxicity. Curr Opin Mol Ther, 6: 600-607, 2004.
42. Rothkamm, K. and Lobrich, M. Evidence for a lack of DNA double-strand break repair in human cells exposed to very low x-ray doses. Proc Natl Acad Sci USA, 100: 5057-5062, 2003.
43. Reddy, M. V. and Randerath, K. Nuclease P1-mediated enhancement of sensitivity of 32P-postlabeling test for structurally diverse DNA adducts. Carcinogenesis, 7: 1543-1551, 1986.
44. Godschalk, R. W., Maas, L. M., Van Zandwijk, N., van't Veer, L. J., Breedijk, A., Borm, P. J., Verhaert, J., Kleinjans, J. C., and van Schooten, F. J. Differences in aromatic-DNA adduct levels between alveolar macrophages and subpopulations of white blood cells from smokers. Carcinogenesis, 19: 819-825, 1998.
45. Vastrik, I., D'Eustachio, P., Schmidt, E., Joshi-Tope, G., Gopinath, G., Croft, D., de Bono, B., Gillespie, M., Jassal, B., Lewis, S., Matthews, L., Wu, G., Birney, E., and Stein, L. Reactome: a knowledge base of biologic pathways and processes. Genome Biol, 8: R39, 2007.
46. Boorsma, A., Foat, B. C., Vis, D., Klis, F., and Bussemaker, H. J. T-profiler: scoring the activity of predefined groups of genes using gene expression data. Nucleic Acids Res, 33: W592-595, 2005.
47. Frueh, F. W., Hayashibara, K. C., Brown, P. O., and Whitlock, J. P., Jr. Use of cDNA microarrays to analyze dioxin-induced changes in human liver gene expression. Toxicol Lett, 122: 189-203, 2001.
48. Kim, W. K., In, Y. J., Kim, J. H., Cho, H. J., Kim, J. H., Kang, S., Lee, C. Y., and Lee, S. C. Quantitative relationship of dioxin-responsive gene expression to dioxin response element in Hep3B and HepG2 human hepatocarcinoma cell lines. Toxicol-Lett, 165: 174-181, 2006.

The invention claimed is:

1. A method for the identification of genotoxic compounds, the method comprising:
   exposing a eukaryotic cell to a potentially genotoxic compound in a culture medium;
   taking a sample from the cell and/or the culture medium at at least one predetermined time point;
   analyzing the sample for increased or decreased expression levels of POLR2D, RAD51, XRCC4, SMUG1, POLR2A, DDB2, MBD4, MAD2L2, ERCC1, ERCC3, REV3L and MGMT as compared to a control cell that is not exposed to the potentially genotoxic compound; and
   identifying the compound as genotoxic based upon the analysis of the expression levels of POLR2D, RAD51, XRCC4, SMUG1, POLR2A, DDB2, MBD4, MAD2L2, ERCC1, ERCC3, REV3L and MGMT.

2. The method according to claim 1, wherein taking a sample from the cell and/or the culture medium at least one predetermined time point comprises taking a sample from the cell and/or the culture medium at more than 1 predetermined time point.

3. The method according to claim 1, wherein taking a sample from the cell and/or the culture medium at least one predetermined time point comprises taking a sample from the cell and/or the culture medium at more than two predetermined time points.

* * * * *

UNITED STATES PATENT AND TRADEMARK OFFICE
CERTIFICATE OF CORRECTION

PATENT NO. : 8,278,044 B2
APPLICATION NO. : 12/998915
DATED : October 2, 2012
INVENTOR(S) : Joseph Catharine Stephanus Kleinjans and Joseph Henri Marie van Delft It is certified that error appears in the above-identified patent and that said Letters Patent is hereby corrected as shown below:

On the title page:
In ITEM (75) Inventors: change "Joseph Henri Marie Delft," to --Joseph Henri Marie van Delft,--

In ITEM (57) ABSTRACT:
    $7^{th}$ line of Abstract      change "medium at least" to --medium at at least--

In ITEM (56) References Cited:
    OTHER PUBLICATIONS
    Page 1, $2^{nd}$ column, $1^{st}$ line of the
        $7^{th}$ entry (line 28),      change "Van Delft et al.," to --van Delft et al.,--

In the specification:

| | | |
|---|---|---|
| COLUMN 3, | LINE 50, | change "(She SH2-domain" to --(Shc SH2-domain-- |
| COLUMN 3, | LINE 57, | change "(Cyclin Gl)" to --(Cyclin G1)-- |
| COLUMN 3, | LINE 67, | change "Fbxo5" to --F-box 5-- |
| COLUMN 4, | LINE 3, | change "6530401 L14" to --6530401L14-- |
| COLUMN 8, | LINE 15, | change "[WAT IS DIT??] show" to --show-- |
| COLUMN 13, | LINE 5, | change "on cover slils" to --on coverslips-- |
| COLUMN 15, | LINE 2, | change "Rctions were" to --Reactions were-- |
| COLUMN 19, | LINE 60, | change "Mt, V. M.," to --Arlt, V. M.,-- |

In the claims:

| | | | |
|---|---|---|---|
| CLAIM 2, | COLUMN 20, | LINE 67, | change "medium at least" to --medium at at least-- |
| CLAIM 3, | COLUMN 21, | LINE 5, | change "medium at least" to --medium at at least-- |

Signed and Sealed this
Thirtieth Day of April, 2013

Teresa Stanek Rea
*Acting Director of the United States Patent and Trademark Office*